United States Patent
Gritzky

(10) Patent No.: US 8,636,662 B2
(45) Date of Patent: Jan. 28, 2014

(54) METHOD AND SYSTEM FOR DISPLAYING SYSTEM PARAMETER INFORMATION

(75) Inventor: Arthur Gritzky, Pollham (AT)

(73) Assignee: General Electric Company, Schenectady, NY (US)

( * ) Notice: Subject to any disclaimer, the term of this patent is extended or adjusted under 35 U.S.C. 154(b) by 708 days.

(21) Appl. No.: 12/759,467

(22) Filed: Apr. 13, 2010

(65) Prior Publication Data

US 2011/0251488 A1    Oct. 13, 2011

(51) Int. Cl.
*A61B 8/00*    (2006.01)

(52) U.S. Cl.
USPC .......................................................... 600/437

(58) Field of Classification Search
USPC .......................................................... 600/437
See application file for complete search history.

(56) References Cited

U.S. PATENT DOCUMENTS

| | | | |
|---|---|---|---|
| 5,584,293 A * | 12/1996 | Darrow et al. | 600/410 |
| 5,997,478 A * | 12/1999 | Jackson et al. | 600/437 |
| 6,368,331 B1 * | 4/2002 | Front et al. | 606/130 |
| 7,454,359 B2 | 11/2008 | Rosenfeld et al. | |
| 8,235,900 B2 * | 8/2012 | Hao | 600/437 |
| 2005/0177400 A1 | 8/2005 | Rosenfeld et al. | |
| 2005/0187796 A1 | 8/2005 | Rosenfeld et al. | |
| 2006/0085229 A9 | 4/2006 | Rosenfeld et al. | |
| 2007/0088695 A1 | 4/2007 | Bleyendaal et al. | |
| 2007/0247473 A1 * | 10/2007 | Li | 345/587 |
| 2008/0201174 A1 | 8/2008 | Ramasubramanian et al. | |
| 2008/0243542 A1 | 10/2008 | Hammond et al. | |
| 2008/0255880 A1 | 10/2008 | Beller et al. | |
| 2008/0312963 A1 | 12/2008 | Reiner | |
| 2011/0009694 A1 * | 1/2011 | Schultz et al. | 600/109 |

\* cited by examiner

*Primary Examiner* — Jacqueline Cheng

(57) ABSTRACT

Methods and systems for displaying system parameter information are provided. One method includes determining a value for a system parameter using the ultrasound system and comparing the determined value to a defined value for a system processing guideline using a processor of the ultrasound system. The method further includes providing system parameter confirmation information based on the comparing when the determined value is not within the defined value.

9 Claims, 8 Drawing Sheets

METHOD AND SYSTEM FOR DISPLAYING SYSTEM PARAMETER INFORMATION

BACKGROUND OF THE INVENTION

The subject matter disclosed herein relates generally to methods and systems for displaying system parameter information, and more particularly to displaying system parameter information on a display of an ultrasound imaging system.

Diagnostic medical imaging systems typically include a scan portion and a control portion having a display. For example, ultrasound imaging systems usually include ultrasound scanning devices, such as ultrasound probes having transducers that are connected to an ultrasound system to control the acquisition of ultrasound data by performing various ultrasound scans (e.g., imaging a volume or body). The ultrasound systems are controllable to operate in different modes of operation and to perform different scans. The acquired ultrasound data then may be displayed, which may include images of a region of interest.

In order to ensure that clinically relevant information is determined, for example to ensure that proper measurements are obtained from a displayed image, certain system parameters may have to be set within predefined ranges or at predefined levels. For example, guidelines exist for use when performing certain measurements based on acquired ultrasound data or displayed images, such as nuchal translucency (NT) measurements.

Conventional methods for confirming systems parameters, which may include confirming that the parameters satisfy certain standards or guidelines, requires user intervention and interaction with the system. For example, a user may have to manually perform actions, such as measurement operations to confirm that system settings are within the defined standards or guidelines. The process performed by the user, often requiring several steps and/or iterations, may have to be performed numerous times in a single day and can be very time consuming. Accordingly, workflow or throughput is decreased as a result of the user required actions.

BRIEF DESCRIPTION OF THE INVENTION

In accordance with various embodiments, a method for providing ultrasound system parameter confirmation information includes determining a value for a system parameter using the ultrasound system and comparing the determined value to a defined value for a system processing guideline using a processor of the ultrasound system. The method further includes providing system parameter confirmation information based on the comparing when the determined value is not within the defined value.

In accordance with other various embodiments, a method for confirming system parameters for ultrasound measurements includes identifying one of a requirement or guideline for a measurement to be performed by an ultrasound imaging system using a processor of the ultrasound system. The method further includes determining at least one system parameter value corresponding to the requirement or guideline based on a user interface selected for operation of the ultrasound system. The method also includes comparing the system parameter value to the requirement or guideline automatically and using the ultrasound system to confirm that the system parameter value is within a defined value for the requirement or guideline.

In accordance with yet other various embodiments, an ultrasound system is provided that includes an ultrasound probe for acquiring ultrasound data for an object of interest and a user input for selecting a user interface. The ultrasound system further includes a system parameter confirmation module configured to confirm that a system parameter is within one of a guideline or requirement for an ultrasound measurement for the selected user interface, and generate an indicator for display. The ultrasound system also includes a display for displaying the indicator when the system parameter is not within the guideline or requirement.

DETAILED DESCRIPTION OF THE INVENTION

Figure 1:
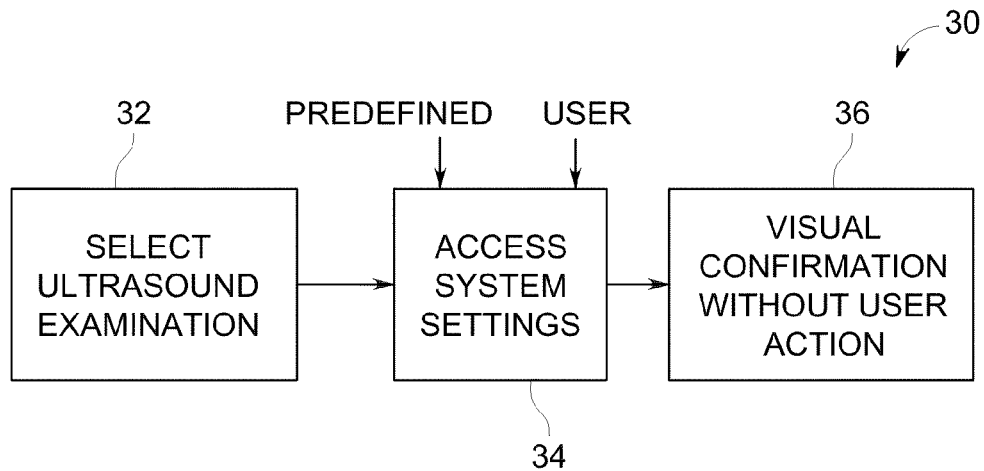
FIG. 1 is a block diagram illustrating a workflow in accordance with various embodiments.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide a system and method for displaying system parameter information on a display of a diagnostic imaging system, especially an ultrasound imaging system, which information may include an indication or confirmation as to whether operating requirements or guidelines, such as for a particular examination, are not satisfied or are satisfied. By practicing various embodiments, a user does not have to manually confirm system settings, for example, by performing different measurements on displayed data. A technical effect of at least one embodiment is reduced examination and workflow time.

One embodiment of a workflow 30 as illustrated in FIG. 1 may be provided to automatically determine system parameters and also to confirm to a user, without user action, whether the system parameters are within certain guidelines or measurement requirements. For example, the workflow 30 can automatically confirm that a particular system parameter setting is within a defined value range. The workflow 30 includes the selection of an ultrasound examination at 32. This selection may include a user selecting a particular imaging scan or measurement to be performed. For example, in ultrasound systems, certain measurements may be performed using acquired image data, such as nuchal translucency (NT) measurements of an imaged fetus or artery measurements, among others. The selection of the ultrasound examination or measurement results in a mode of operation being selected, which may include a particular scanning mode or a particular processing or display mode.

With the ultrasound examination or measurement selected, system settings, for example, image parameter settings, corresponding to the selection are accessed at 34. The system settings may be predefined based on the selection of the examination or measurement, based on a user setting, based on acquired image data, etc. For example, a user may be displaying a zoomed (enlarged) fetal image for review and performing NT measurements. The user interface for the NT measurements in various embodiments allows a user to measure a fetal crown-rump length based on displayed markers or calipers positioned by a user. The displayed image of the fetus, which may be a still image from a cine loop, is displayed at a certain resolution level, which may be based on predefined settings, user settings (such as a user zooming in to mark the crown-rump length) or the image acquisition settings. The resolution is defined by a pixel size, which is one of the system settings that is accessed. Other system settings may be accessed and include, but are not limited to, frequency, image mode, etc. It should be noted that the accessed system settings may include some or all of the system settings for a particular mode of operation. For example, the system parameters accessed may correspond to only those parameters that need to be confirmed to ensure proper subsequent processing, such as a maximum pixel size to be used for subsequent processing to perform NT measurements.

Once the system settings have been accessed, a visual confirmation is provided at 36 without user action. Thus, the system automatically determines certain system parameters and in various embodiments confirms the system parameters, such as with a visual indication on a display of the ultrasound system. The confirmation of one or more system settings and the display of the confirmation are performed without any user action. For example, when performing NT measurements, before a user selects the landmarks to define the crown-rump length, a maximum pixel size must be confirmed to ensure compliance with NT measurement guidelines. For example, the magnification or zoom level of the displayed fetal image used to perform the NT measurements should have a pixel size that is no greater than 0.1 millimeters (mm).

By accessing the system parameters, at 34, a determination can automatically be made as to the current pixel size setting, which value is then compared to the guideline value (e.g., maximum pixel size). Based on the comparison, a visual indicator may be displayed to user as to whether the pixel size is within the guideline. For example, text or color coding may be provided on the image as described in more detail herein.

In some embodiments, a visual indication is displayed only if the system parameter, such as the pixel size, is not within the guideline. In other embodiments, the visual indication may be displayed when the system parameter is within the guideline or when there is no guideline.

Thus, using the automated workflow 30, a user does not have to manually determine particular system settings. For example, in NT measurements, a user does not have to first manually set markers to measure the size of a pixel in the displayed image. Accordingly, no user action is needed to confirm system settings. A quality control mechanism is thereby provided.

Figure 2:
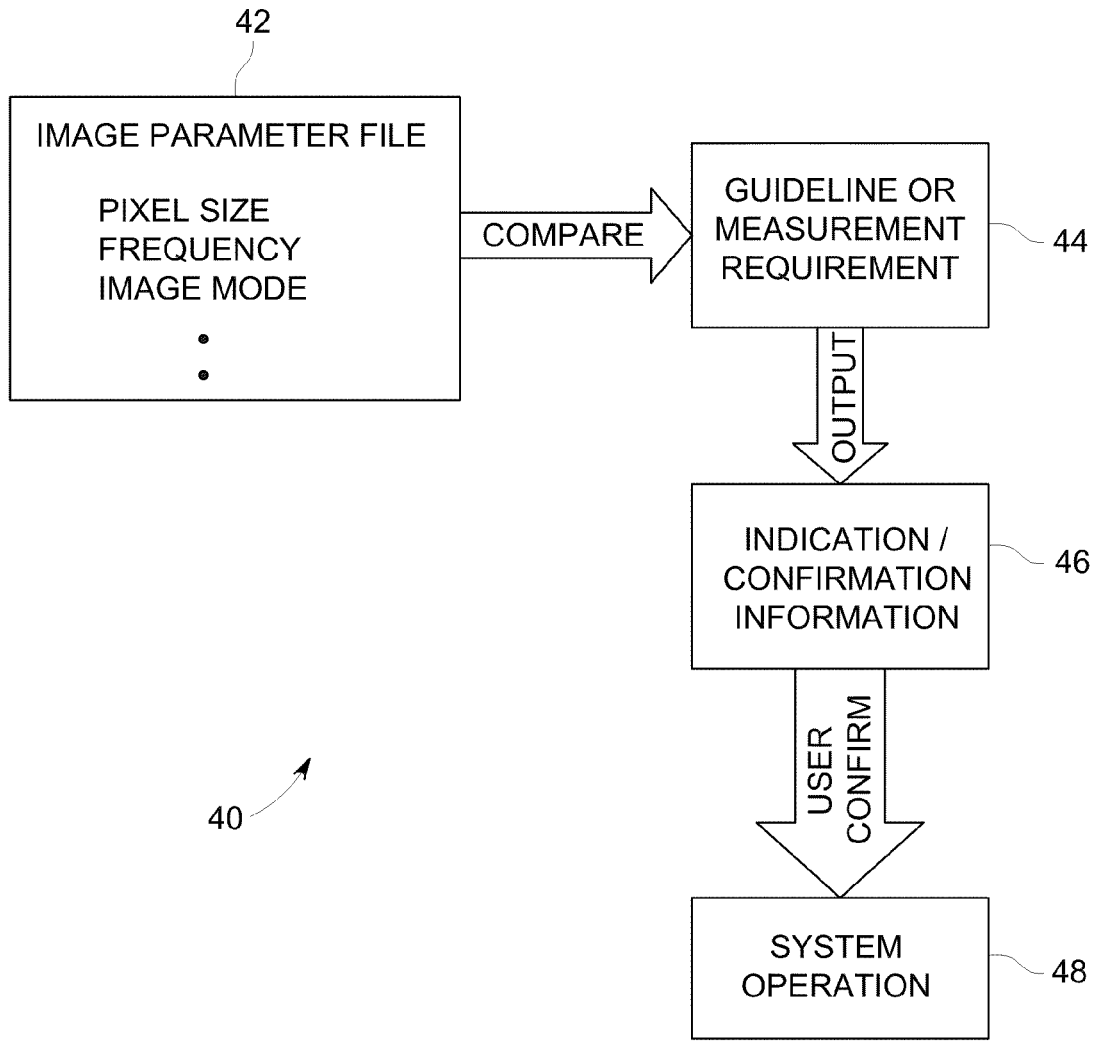
FIG. 2 is a block diagram illustrating a process for confirming system parameters in accordance with various embodiments.

Accordingly, system parameters may be accessed and optionally evaluated using a process 40 as illustrated in FIG. 2. More particularly, an image parameter file 42, which generally may be memory locations storing system parameter information or a separately generated file, contains system setting information. The image parameter file 42 in this example includes image parameter settings, such as particular values for one or more image parameters. The parameters may include, for example, pixel size, frequency and imaging mode, among others. The parameters may be settings that are stored in known locations within the ultrasound system or may be acquired from the current operation of the system.

As part of the process 40, the values or settings of the parameters are compared to a guideline or measurement requirement 44 as described in more detail herein. It should be noted that the guideline or measurement requirement 44 may be based on an industry standard, based on a mode of operation, based on user defined settings, etc. Accordingly, the guideline or measurement requirement 44 may be preset, predefined and/or configurable by a user.

The comparison is then used to generate an output of indication or confirmation information that is presented to a user. For example, indication information 46 may be output to a user, which may include visual (e.g., text or color coding) and/or audible indications that a particular system setting is not within or does not comply with the guideline or measurement requirement. A user may then adjust the system settings until no indication is provided (which corresponds to the setting being within the guideline or measurement requirement) or optionally until confirmation is displayed that the setting is within the guideline or measurement requirement and visually confirmed by the user as acceptable. Thereafter, a system operation 48 may be initiated, for example, after landmarks in a fetal image are identified, an NT measurement may be initiated. The user may change one or more system settings, for example, a zoom level, before the system operation 48 is performed if the confirmation information 46 indicates that one or more parameters of interest do not have settings that are within the guideline or measurement requirement 44. It should be noted that in some embodiments, the system parameter information is displayed without performing the comparison.

Figure 3:
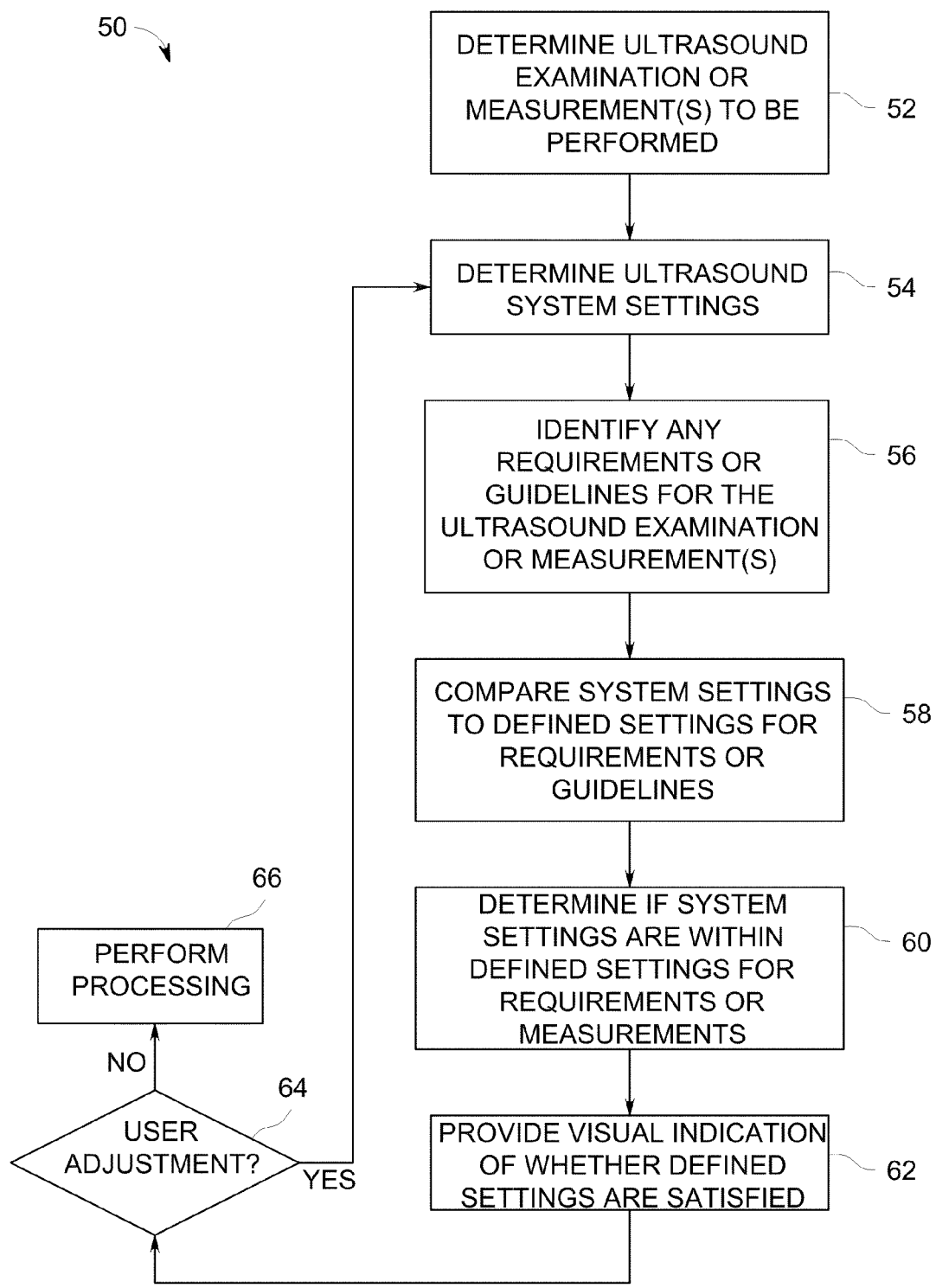
FIG. 3 is a flowchart of a method for providing system parameter confirmation information in accordance with various embodiments.

Thus, a method 50 as illustrated in FIG. 3 may be provided in accordance with at least one embodiment of the invention. The method 50 allows a user to confirm, for example, visually confirm based on displayed information or the lack of displayed information (e.g., no displayed indication that the system setting is not within a guideline), a system setting, which may include visually determining that displayed information or lack thereof indicates that a value of the system setting is at or within a predetermined or predefined value. A user is able to confirm system settings without having to perform further actions, such as manually measuring or identifying portions of an image to determine the system settings.

Figure 4:
FIG. 4 is a screenshot of a user interface having a confirmation indicator provided in accordance with various embodiments.

The method 50 includes determining at 52 an ultrasound examination or measurement(s) to be performed as described in more detail herein. For example, based on a user input or mode of operation, the ultrasound examination or measurement(s) to be performed may be identified. In some embodiments, the ultrasound examination or measurement(s) to be performed may be determined based on a selected user interface, such as the NT measurement interface 70 illustrated in FIG. 4, showing a screenshot with a fetal image displayed. Thus, the ultrasound examination or measurement(s) to be performed may be based on the mode of operation, as well as the type of operation to be performed.

In this example, the user interface provided corresponds to an Early Gestation mode of operation, which may be selected using one of a plurality of user selectable selection elements 72 illustrated as virtual buttons on the user interface 70. The selection elements 72 are selectable by a user interface selection device, such as keyboard or mouse of the ultrasound system as described in more detail below. In the illustrated embodiment, the Early Gest. selection element 72 is selected, which may be indicated by highlighting or coloring the selection element 72 or the border thereof, and results in various options for the user interface 70 being displayed for this mode of operation, which may include measurement selection elements 74 corresponding to different measurement operations that may be performed in this mode of operation, namely the Early Gestation mode of operation. In the illustrated embodiment, an NT measurement is selected, which allows a user to, among other things, identify landmarks in the displayed image 76, which is a saggital section view of a fetus. For example, a user may use the keyboard or mouse of the ultrasound system to mark two points (not shown) on the image 76 that identify the fetal crown-rump length. As described in more detail herein, in order to properly measure the length of the fetal crown-rump, the resolution of the displayed image 76 should be no more than 0.1 mm, which corresponds to a pixel size of no more than 0.1 mm.

It should be noted that a user interface selection device 78 also may be used to select selection elements and/or mark landmarks on the image 76. The user interface selection device 78 is essentially a virtual selection element, which may include, for example, a virtual cursor button 80 and set buttons 82. It also should be noted that additional selectable elements 84 and operations may be provided by the user interface 70, for example, printing, freezing an image for display such, as from a cine loop, determining the type of image to be displayed and exiting the user interface 70, among others. Further, identification information 86 also may be displayed that provides information regarding the displayed image 76, such as the date and time the image 76 was acquired.

Referring again to the method 50 of FIG. 3, after the ultrasound examination or measurement(s) to be performed are determined, ultrasound system settings are determined at 54 as described in more detail herein. The system settings may include image parameter values corresponding to a displayed image, such as the image 76 (shown in FIG. 4). The parameter values may be based on the image being displayed. For example, a pixel size value may be determined based on the current resolution or zoom level of the displayed image. The parameter values are values that have been set by a user, preset based on the mode of operation, or set based on a user input (e.g., based on a level of image zoom), among others. The parameter values may be values that are accessible within the ultrasound system or derived from the current operating settings of the ultrasound system.

Thereafter, requirements or guidelines for the ultrasound examination or measurement(s) are identified at 56. In some embodiments, the identification of the requirements or guidelines may be based on the user interface initiated by the user and the corresponding operations or processing to be performed using that interface. For example, if the user interface 70 (shown in FIG. 4) is initiated (or selected) by the user, then any requirements or guidelines for NT measurements using ultrasound data are identified, which as described in more detail herein, would include an identification of a maximum pixel size to ensure proper measurements in the range of pixel resolution. In some embodiments, no requirements or guidelines may correspond to the particular imaging mode or measurements to be performed using a selected user interface. In such case, one or more system settings may still be displayed to the user. In general, various embodiments identify one or more requirements or guidelines (whether predefined or user defined) that may affect subsequent processing or that are needed to ensure proper calculations or measurements based on ultrasound image data, such as displayed image data.

Thereafter, at 58 the determined system settings, such as the current system parameter values may be compared to the values for the requirements or guidelines. For example, a current pixel size, frequency value or operating mode may be compared to defined or required values based on requirements or guidelines. The comparison is a check of the system parameters, for example, a check of the image parameters. In particular, based on the comparison, a determination is made at 60 as to whether the system settings are within the defined settings for the requirements or guidelines. For example, if a maximum value or range of values is defined by the requirements or guidelines, a determination is made as to whether the system value is within the maximum value or range of values.

Based on the determination, a visual indication is provided at 62. For example, a visual indication is provided as to whether the defined settings for the requirements or guidelines are satisfied, such as whether the current parameter value(s) is within the defined or required value(s). The visual indication may be displayed as text and/or color. For example, an indicator 90 (as shown in FIG. 4) may be provided that includes text identifying the system parameter that was evaluated and providing an indication whether the system parameter value is within the requirements or guidelines. For example, as shown in FIG. 4, colored text (e.g., red colored text) may indicate for NT measurements that the "current measurement magnification is too low" and to "please zoom image." Thus, the indicator 90 (which also may be referred to as a confirmation indicator) identifies the system parameter being confirmed, whether the corresponding requirement or guideline is satisfied and further action that is needed to satisfy the requirement or guideline. Thus, by viewing the indicator 90, a user is able to determine whether current settings, for example, a current zoom level is sufficient to perform subsequent processing operations, such as NT measurements. It should be noted, and as described in more detail herein, any system parameter may be determined and confirmed. For example, if the subsequent processing includes performing plaque measurements that compares two distances, a zoom level may be determined, such as based on pixel size, to ensure proper measurements.

It further should be noted that the indicator 90 may be only text, only a color indication (e.g. a colored icon) or a combination of text and color. Additionally, the indicator 90 in some embodiments is only displayed when the system parameter does not satisfy the requirement or guideline and further action is needed.

Referring again to FIG. 3, a determination is made at 64 as to whether a system setting should be changed, for example, user adjusted. The determination may be made automatically or by a user based on the displayed indicator 90, or in some embodiments, the lack thereof. If the indicator 90 indicates that the requirement(s) or guideline(s) value(s) are satisfied (confirmed) or if no indicator is displayed, then processing, for example, image processing may be performed at 66. For example, and continuing with the NT measurement embodiment, a user may then identify landmarks or points on the image (e.g., fetal crown-rump length endpoints) and initiate measurement of the fetal crown-rump length. If the indicator 90 indicates that the requirement(s) or guideline(s) value(s) are not satisfied, such as not within required value(s), then a user may adjust one or more system parameters (e.g., zoom level) after which the adjusted system settings are determined at 54.

Thus, in accordance with various embodiments, automatic determination of one or more system parameters is provided, which may also include confirmation of the parameter(s). Also, confirmation may be provided as to whether the system parameter(s) is within a particular range or within a defined value and without user action such that subsequent processing may be properly performed. Moreover, system parameter information, indication information or confirmation information displayed to the user in various embodiments may include parameter values not normally displayed to a user, for example, pixel size or confirmation of pixel size.

Figure 5:
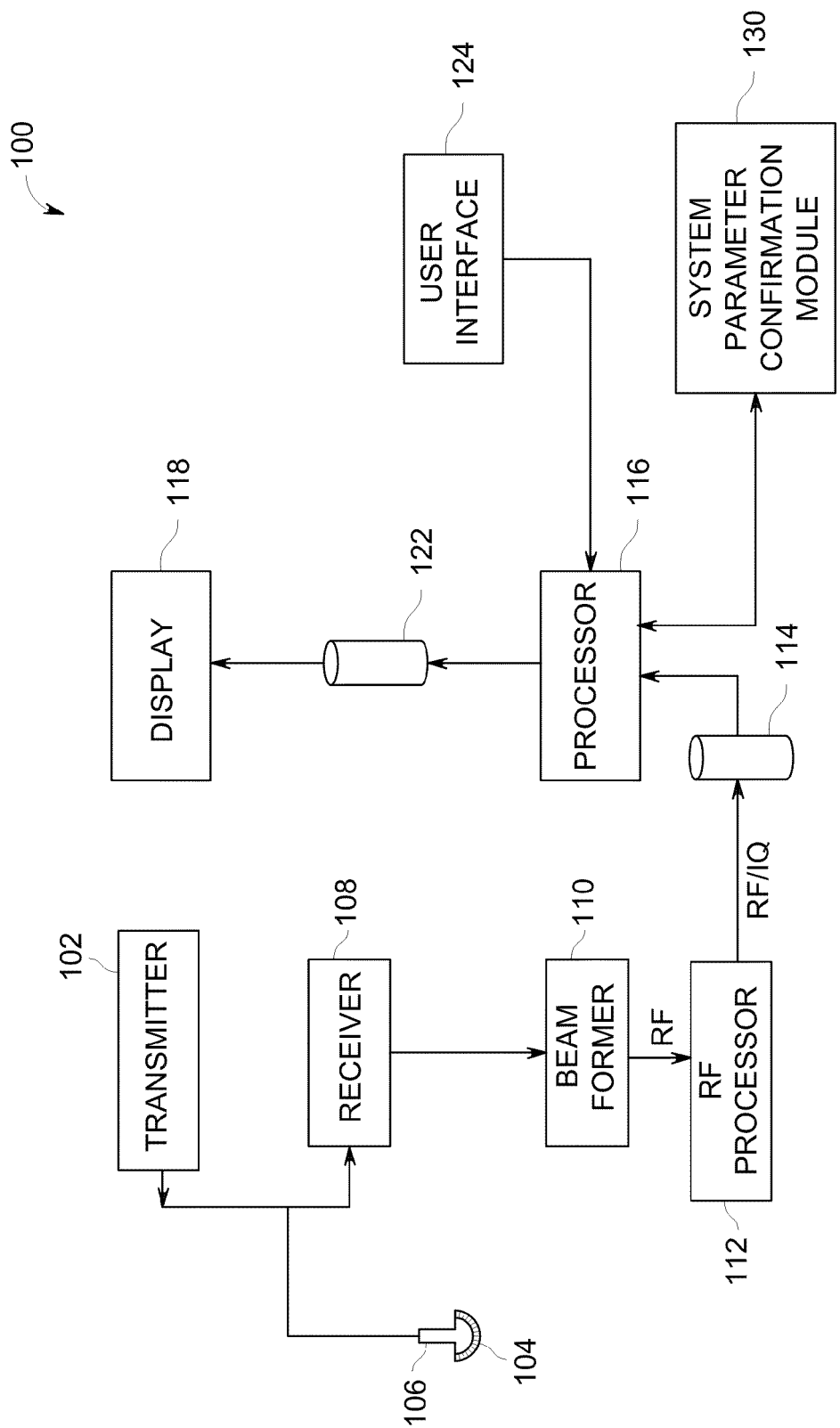
FIG. 5 is a block diagram of a diagnostic imaging system including a system parameter confirmation module in accordance with various embodiments.

Various embodiments, including the method 50 may be implemented in an ultrasound system 100 as shown in FIG. 5, which is a block diagram of the ultrasound system 100. The ultrasound system 100 is capable of electrical or mechanical steering of a soundbeam (such as in 3D space) and is configurable to acquire information corresponding to a plurality of 2D representations or images of a region of interest (ROI) in a subject or patient, which may be defined or adjusted as described in more detail herein. The ultrasound system 100 is configurable to acquire 2D images in one or more planes of orientation.

The ultrasound system 100 includes a transmitter 102 that, under the guidance of a beamformer 110, drives an array of elements 104 (e.g., piezoelectric elements) within a probe 106 to emit pulsed ultrasonic signals into a body. A variety of geometries may be used. The ultrasonic signals are backscattered from structures in the body, like blood cells or muscular tissue, to produce echoes that return to the elements 104. The echoes are received by a receiver 108. The received echoes are passed through the beamformer 110, which performs receive beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to a memory 114 for storage.

In the above-described embodiment, the beamformer 110 operates as a transmit and receive beamformer. In an alternative embodiment, the probe 106 includes a 2D array with sub-aperture receive beamforming inside the probe. The beamformer 110 may delay, apodize and sum each electrical signal with other electrical signals received from the probe 106. The summed signals represent echoes from the ultrasound beams or lines. The summed signals are output from the beamformer 110 to an RF processor 112. The RF processor 112 may generate different data types, e.g. B-mode, color Doppler (velocity/power/variance), tissue Doppler (velocity), and Doppler energy, for multiple scan planes or different scanning patterns. For example, the RF processor 112 may generate tissue Doppler data for multi-scan planes. The RF processor 112 gathers the information (e.g. I/Q, B-mode, color Doppler, tissue Doppler, and Doppler energy information) related to multiple data slices and stores the data information, which may include time stamp and orientation/rotation information, in the memory 114.

The ultrasound system 100 also includes a processor 116 to process the acquired ultrasound information (e.g., RF signal data or IQ data pairs) and prepare frames of ultrasound information for display on display 118. The processor 116 is adapted to perform one or more processing operations according to a plurality of selectable ultrasound modalities on the acquired ultrasound data. Acquired ultrasound data may be processed and displayed in real-time during a scanning session as the echo signals are received. Additionally or alternatively, the ultrasound data may be stored temporarily in memory 114 during a scanning session and then processed and displayed in an off-line operation.

The processor 116 is connected to a user interface 124 (which may include a mouser, keyboard, etc.) that may control operation of the processor 116 as explained below in more detail. A display 118 includes one or more monitors that present patient information, including diagnostic ultrasound images to the user for diagnosis and analysis. One or both of memory 114 and memory 122 may store two-dimensional (2D) or three-dimensional (3D) data sets of the ultrasound data, where such 2D and 3D data sets are accessed to present 2D (and/or 3D images). The images may be modified and the display settings of the display 118 also manually adjusted using the user interface 124.

A system parameter confirmation module 130 is also provided and connected to the processor 116. In some embodiments, the system parameter confirmation module 130 may be software running on the processor 116 or hardware provided as part of the processor 116. The system parameter confirmation module 130 identifies and confirms system parameter settings as described in more detail herein.

It should be noted that although the various embodiments may be described in connection with an ultrasound system, the methods and systems are not limited to ultrasound imaging or a particular configuration thereof. The various embodiments may be implemented in connection with different types of imaging systems, including, for example, x-ray imaging systems, magnetic resonance imaging (MRI) systems, computed-tomography (CT) imaging systems, positron emission tomography (PET) imaging systems, or combined imaging systems, among others. Further, the various embodiments may be implemented in non-medical imaging systems, for example, non-destructive testing systems such as ultrasound weld testing systems or airport baggage scanning systems.

Figure 6:
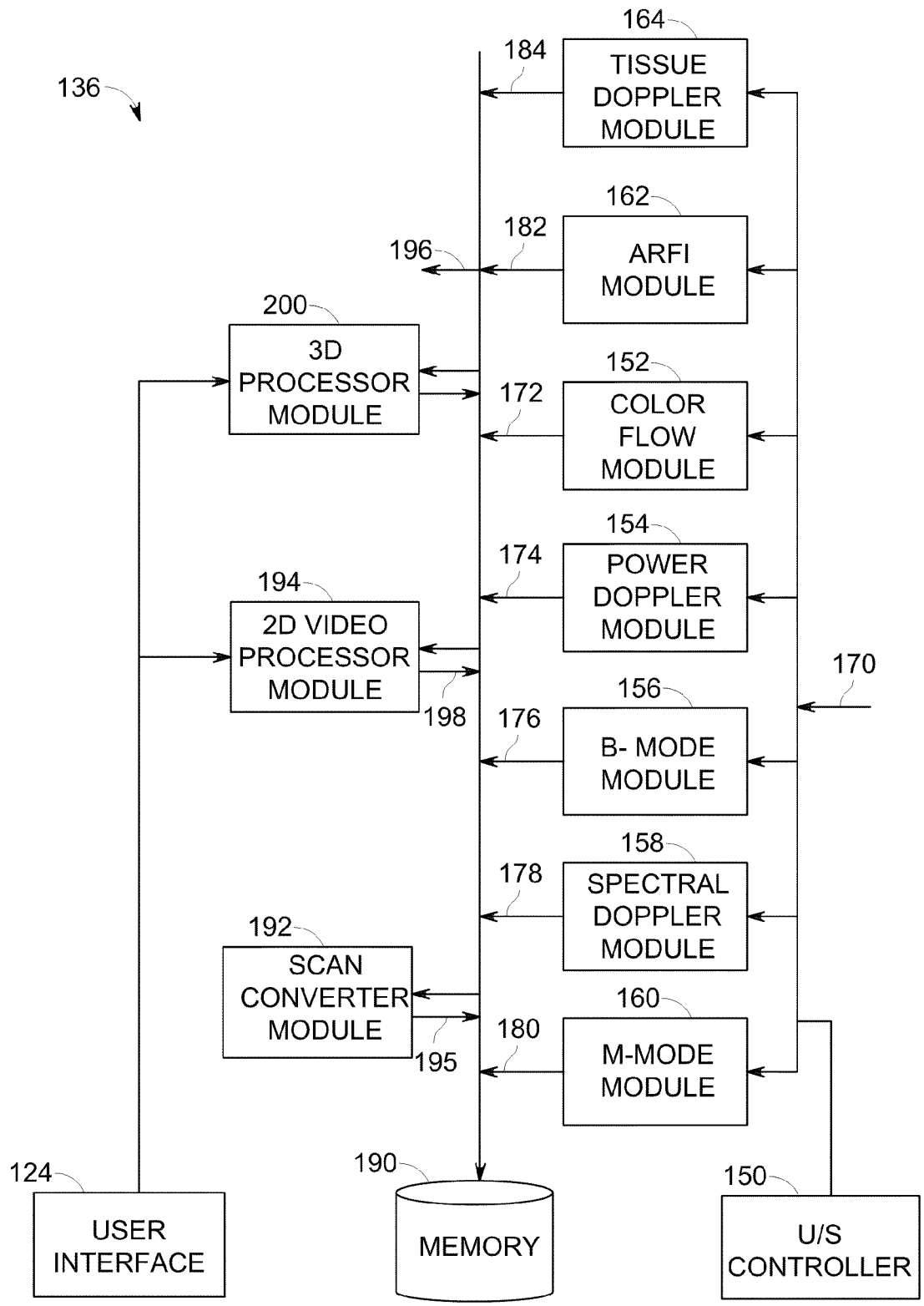
FIG. 6 is a block diagram of an ultrasound processor module of the diagnostic imaging system of FIG. 5 formed in accordance with various embodiments.

FIG. 6 illustrates an exemplary block diagram of an ultrasound processor module 136, which may be embodied as the processor 116 of FIG. 5 or a portion thereof. The ultrasound processor module 136 is illustrated conceptually as a collection of sub-modules, but may be implemented utilizing any combination of dedicated hardware boards, DSPs, processors, etc. Alternatively, the sub-modules of FIG. 10 may be implemented utilizing an off-the-shelf PC with a single processor or multiple processors, with the functional operations distributed between the processors. As a further option, the sub-modules of FIG. 6 may be implemented utilizing a hybrid configuration in which certain modular functions are performed utilizing dedicated hardware, while the remaining modular functions are performed utilizing an off-the shelf PC and the like. The sub-modules also may be implemented as software modules within a processing unit.

The operations of the sub-modules illustrated in FIG. 6 may be controlled by a local ultrasound controller 150 or by the processor module 136. The sub-modules 152-164 perform mid-processor operations. The ultrasound processor module 136 may receive ultrasound data 170 in one of several forms. In the embodiment of FIG. 6, the received ultrasound data 170 constitutes I,Q data pairs representing the real and imaginary components associated with each data sample. The I,Q data pairs are provided to one or more of a color-flow sub-module 152, a power Doppler sub-module 154, a B-mode sub-module 156, a spectral Doppler sub-module 158 and an M-mode sub-module 160. Optionally, other sub-modules may be included such as an Acoustic Radiation Force Impulse (ARFI) sub-module 162 and a Tissue Doppler (TDE) sub-module 164, among others.

Each of sub-modules 152-164 are configured to process the I,Q data pairs in a corresponding manner to generate color-flow data 172, power Doppler data 174, B-mode data 176, spectral Doppler data 178, M-mode data 180, ARFI data 182, and tissue Doppler data 184, all of which may be stored in a memory 190 (or memory 114 or memory 122 shown in FIG. 5) temporarily before subsequent processing. For example, the B-mode sub-module 156 may generate B-mode data 176 including a plurality of B-mode image planes, such as in a biplane or triplane image acquisition as described in more detail herein.

The data 172-184 may be stored, for example, as sets of vector data values, where each set defines an individual ultrasound image frame. The vector data values are generally organized based on the polar coordinate system.

A scan converter sub-module 192 accesses and obtains from the memory 190 the vector data values associated with an image frame and converts the set of vector data values to Cartesian coordinates to generate an ultrasound image frame 195 formatted for display. The ultrasound image frames 195 generated by the scan converter module 192 may be provided back to the memory 190 for subsequent processing or may be provided to the memory 114 or the memory 122.

Once the scan converter sub-module 192 generates the ultrasound image frames 195 associated with, for example, B-mode image data, and the like, the image frames may be restored in the memory 190 or communicated over a bus 196 to a database (not shown), the memory 114, the memory 122 and/or to other processors.

The scan converted data may be converted into an X,Y format for video display to produce ultrasound image frames. The scan converted ultrasound image frames are provided to a display controller (not shown) that may include a video processor that maps the video to a grey-scale mapping for video display. The grey-scale map may represent a transfer function of the raw image data to displayed grey levels. Once the video data is mapped to the grey-scale values, the display controller controls the display 118 (shown in FIG. 5), which may include one or more monitors or windows of the display, to display the image frame. The image displayed in the display 118 is produced from image frames of data in which each datum indicates the intensity or brightness of a respective pixel in the display.

Referring again to FIG. 6, a 2D video processor sub-module 194 combines one or more of the frames generated from the different types of ultrasound information. For example, the 2D video processor sub-module 194 may combine a different image frames by mapping one type of data to a grey map and mapping the other type of data to a color map for video display. In the final displayed image, color pixel data may be superimposed on the grey scale pixel data to form a single multi-mode image frame 198 (e.g., functional image) that is again re-stored in the memory 190 or communicated over the bus 196. Successive frames of images may be stored as a cine loop in the memory 190 or memory 122 (shown in FIG. 5). The cine loop represents a first in, first out circular image buffer to capture image data that is displayed to the user. The user may freeze the cine loop by entering a freeze command at the user interface 124. The user interface 124 may include, for example, a keyboard and mouse and all other input controls associated with inputting information into the ultrasound system 100 (shown in FIG. 5).

A 3D processor sub-module 200 is also controlled by the user interface 124 and accesses the memory 190 to obtain 3D ultrasound image data and to generate three dimensional images, such as through volume rendering or surface rendering algorithms as are known. The three dimensional images may be generated utilizing various imaging techniques, such as ray-casting, maximum intensity pixel projection and the like.

Figure 7:
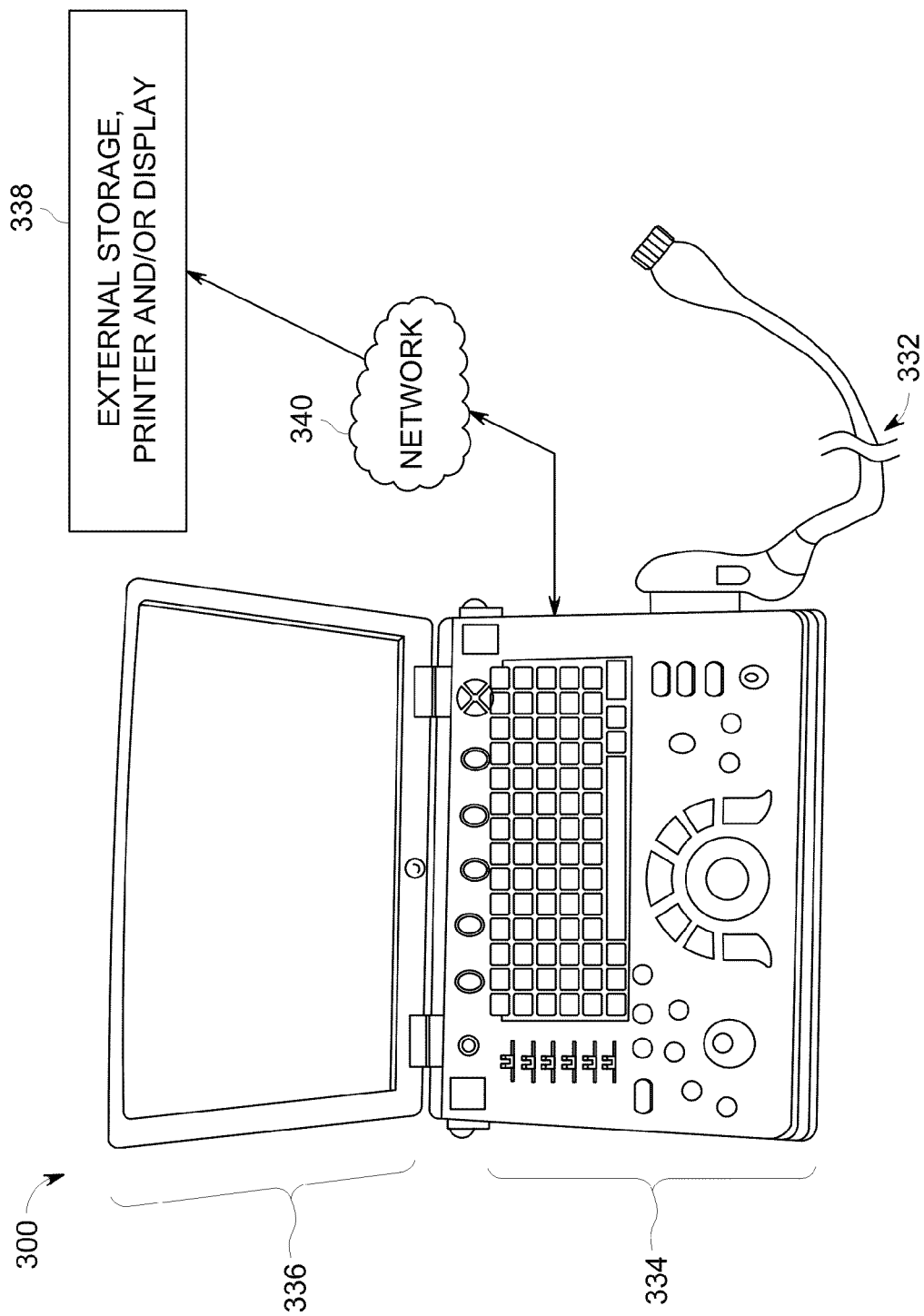
FIG. 7 is a diagram illustrating a 3D capable miniaturized ultrasound system in which various embodiments may be implemented.
Figure 8:
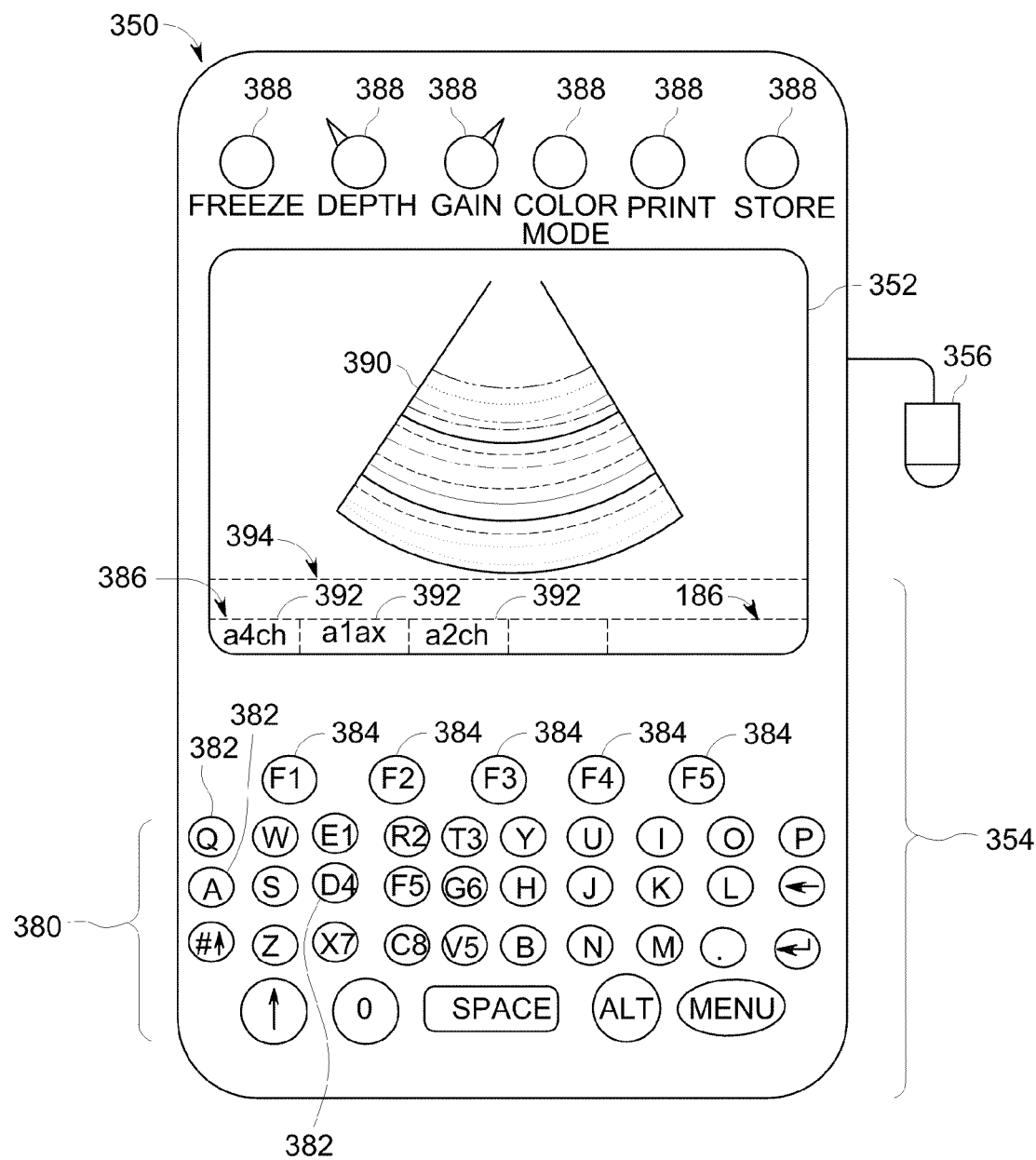
FIG. 8 is a diagram illustrating a 3D capable hand carried or pocket-sized ultrasound imaging system in which various embodiments may be implemented.
Figure 9:
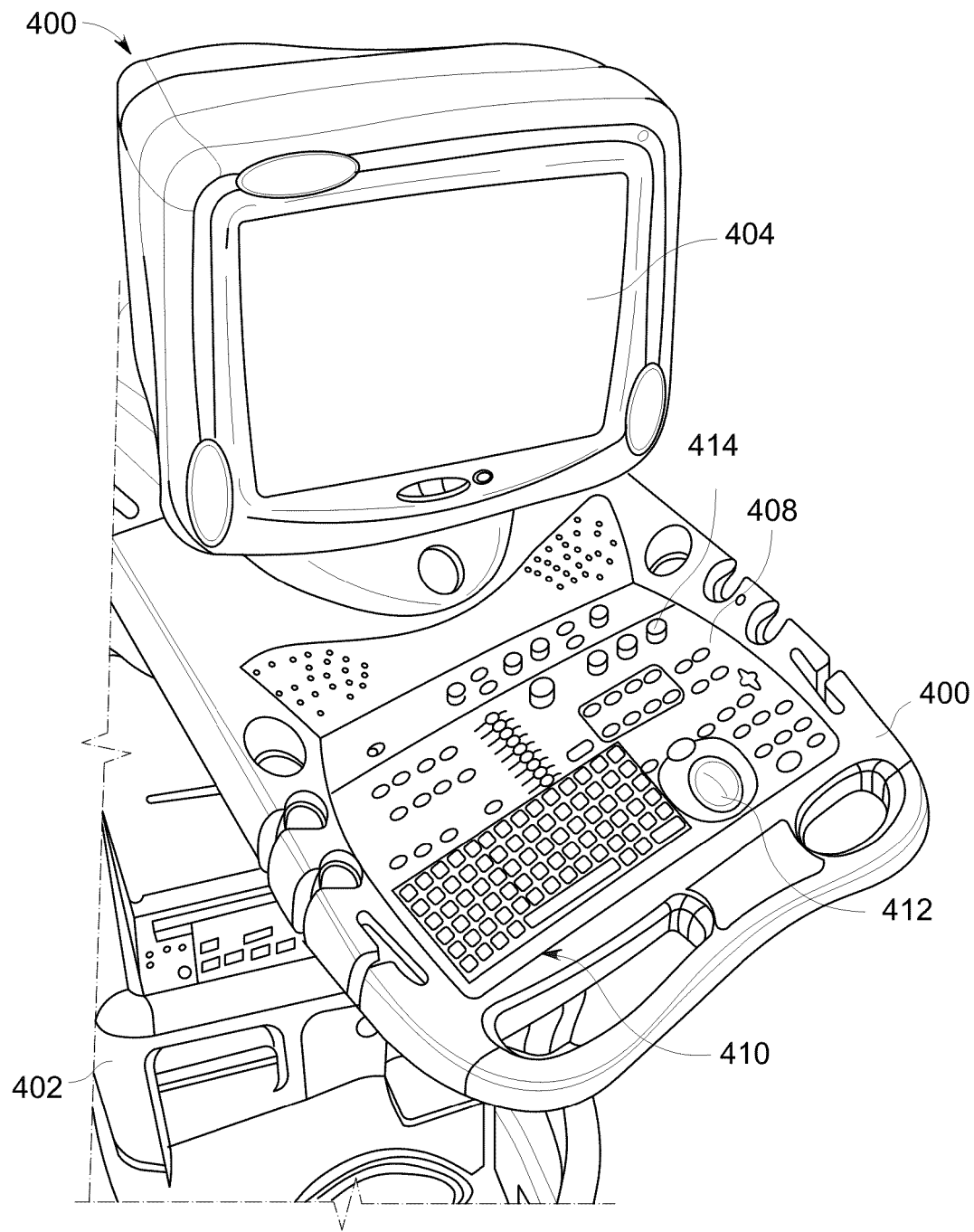
FIG. 9 is a diagram illustrating a 3D capable console type ultrasound imaging system in which various embodiments may be implemented.

The ultrasound system 100 of FIG. 5 may be embodied in a small-sized system, such as laptop computer or pocket sized system as well as in a larger console-type system. FIGS. 7 and 8 illustrate small-sized systems, while FIG. 9 illustrates a larger system.

FIG. 7 illustrates a 3D-capable miniaturized ultrasound system 300 having a probe 332 that may be configured to acquire 3D ultrasonic data or multi-plane ultrasonic data. For example, the probe 332 may have a 2D array of elements 104 as discussed previously with respect to the probe 106 of FIG. 5. A user interface 334 (that may also include an integrated display 336) is provided to receive commands from an operator. As used herein, "miniaturized" means that the ultrasound system 330 is a handheld or hand-carried device or is configured to be carried in a person's hand, pocket, briefcase-sized case, or backpack. For example, the ultrasound system 330 may be a hand-carried device having a size of a typical laptop computer. The ultrasound system 330 is easily portable by the operator. The integrated display 336 (e.g., an internal display) is configured to display, for example, one or more medical images.

The ultrasonic data may be sent to an external device 338 via a wired or wireless network 340 (or direct connection, for example, via a serial or parallel cable or USB port). In some embodiments, the external device 338 may be a computer or a workstation having a display, or the DVR of the various embodiments. Alternatively, the external device 338 may be a separate external display or a printer capable of receiving image data from the hand carried ultrasound system 330 and of displaying or printing images that may have greater resolution than the integrated display 336.

FIG. 8 illustrates a hand carried or pocket-sized ultrasound imaging system 350 wherein the display 352 and user interface 354 form a single unit. By way of example, the pocket-sized ultrasound imaging system 350 may be a pocket-sized or hand-sized ultrasound system approximately 2 inches wide, approximately 4 inches in length, and approximately 0.5 inches in depth and weighs less than 3 ounces. The pocket-sized ultrasound imaging system 350 generally includes the display 352, user interface 354, which may or may not include a keyboard-type interface and an input/output (I/O) port for connection to a scanning device, for example, an ultrasound probe 356. The display 352 may be, for example, a 320×320 pixel color LCD display (on which a medical image 390 may be displayed). A typewriter-like keyboard 380 of buttons 382 may optionally be included in the user interface 354.

Multi-function controls 384 may each be assigned functions in accordance with the mode of system operation (e.g., displaying different views). Therefore, each of the multi-function controls 384 may be configured to provide a plurality of different actions. Label display areas 386 associated with the multi-function controls 384 may be included as necessary on the display 352. The system 350 may also have additional keys and/or controls 388 for special purpose functions, which may include, but are not limited to "freeze," "depth control," "gain control," "color-mode," "print," and "store."

One or more of the label display areas 386 may include labels 392 to indicate the view being displayed or allow a user to select a different view of the imaged object to display. The selection of different views also may be provided through the associated multi-function control 384. The display 352 may also have a textual display area 394 for displaying information relating to the displayed image view (e.g., a label associated with the displayed image).

It should be noted that the various embodiments may be implemented in connection with miniaturized or small-sized ultrasound systems having different dimensions, weights, and power consumption. For example, the pocket-sized ultrasound imaging system 350 and the miniaturized ultrasound system 300 may provide the same scanning and processing functionality as the system 100 (shown in FIG. 5).

FIG. 9 illustrates an ultrasound imaging system 400 provided on a movable base 402. The portable ultrasound imaging system 400 may also be referred to as a cart-based system. A display 404 and user interface 406 are provided and it should be understood that the display 404 may be separate or separable from the user interface 406. The user interface 406 may optionally be a touchscreen, allowing the operator to select options by touching displayed graphics, icons, and the like.

The user interface 406 also includes control buttons 408 that may be used to control the portable ultrasound imaging system 400 as desired or needed, and/or as typically provided. The user interface 406 provides multiple interface options that the user may physically manipulate to interact with ultrasound data and other data that may be displayed, as well as to input information and set and change scanning parameters and viewing angles, etc. For example, a keyboard 410, trackball 412 and/or multi-function controls 414 may be provided.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for providing ultrasound system parameter confirmation information, the method comprising:
   determining a value for a system parameter using the ultrasound system;
   comparing the determined value to a defined value for a system processing guideline using a processor of the ultrasound system; and
   providing system parameter confirmation information based on the comparing when the determined value is not within the defined value, wherein the system parameter confirmation information confirms that the system parameter is sufficient for performing nuchal translucency (NT) measurements with the ultrasound system.

2. A method in accordance with claim 1 further comprising determining an ultrasound examination or measurement to be performed, and wherein the system processing guideline is identified based on the determination of the ultrasound examination or measurement to be performed.

3. A method in accordance with claim 2 further comprising identifying a selected user interface to determine the ultrasound examination or measurement to be performed.

4. A method in accordance with claim 1 wherein the system parameter confirmation information is provided without user action.

5. A method in accordance with claim 1 wherein the system parameter is not normally displayed to a user.

6. A method in accordance with claim 1 wherein the system parameter comprises an image pixel size.

7. A method in accordance with claim 1 wherein the system parameter confirmation information comprises image pixel size information based on a zoom level of a displayed image.

8. A method in accordance with claim 1 further comprising displaying the system parameter confirmation information without input of measurement indicators on a displayed image.

9. A method in accordance with claim 1 wherein the system parameter comprises an image parameter corresponding to one of image pixel size, frequency or image mode.

* * * * *